US012186479B2

(12) United States Patent
 Buchberger

(10) Patent No.: US 12,186,479 B2
(45) Date of Patent: Jan. 7, 2025

(54) AEROSOL DELIVERY DEVICE AND METHOD UTILIZING A FLAVORING RESERVOIR

(71) Applicant: Nicoventures Trading Limited, London (GB)

(72) Inventor: Helmut Buchberger, St. Florian (AT)

(73) Assignee: NICOVENTURES TRADING LIMITED, London (GB)

( * ) Notice: Subject to any disclaimer, the term of this patent is extended or adjusted under 35 U.S.C. 154(b) by 666 days.

(21) Appl. No.: 17/443,170

(22) Filed: Jul. 21, 2021

(65) Prior Publication Data

US 2021/0346620 A1    Nov. 11, 2021

Related U.S. Application Data

(63) Continuation of application No. 16/842,153, filed on Apr. 7, 2020, now Pat. No. 11,116,919, which is a
(Continued)

(30) Foreign Application Priority Data

Aug. 13, 2014    (GB) ...................................... 1414331

(51) Int. Cl.
    | | |
    |---|---|
    | *A24F 13/00* | (2006.01) |
    | *A24F 40/30* | (2020.01) |
    | *A24F 40/40* | (2020.01) |
    | *A24F 40/485* | (2020.01) |
    | *A61M 11/04* | (2006.01) |
    | *A61M 15/00* | (2006.01) |
    (Continued)

(52) U.S. Cl.
CPC ......... *A61M 15/0091* (2013.01); *A24F 40/30* (2020.01); *A24F 40/40* (2020.01); *A24F 40/485* (2020.01); *A61M 11/042* (2014.02); *A61M 15/06* (2013.01); *A24F 40/10* (2020.01); *A24F 40/20* (2020.01); *A61M 15/002* (2014.02); *A61M 15/0021* (2014.02); *A61M 2205/3653* (2013.01); *A61M 2205/588* (2013.01); *A61M 2205/8206* (2013.01)

(58) Field of Classification Search
CPC ........................................................ A24F 47/00
USPC ................................................. 131/328–329
See application file for complete search history.

(56) References Cited

U.S. PATENT DOCUMENTS 2,809,634 A    10/1957 Hirotada et al.
3,356,094 A    12/1967 Drummond et al.
(Continued)

FOREIGN PATENT DOCUMENTS

| CA | 1301010 C | 5/1992 |
|---|---|---|
| CN | 1248888 A | 3/2000 |

(Continued)

OTHER PUBLICATIONS

Celgrad LLC, World Leader in Battery Separator Technology, www.celgard.com, Apr. 17, 2018, 6 pages.
(Continued)

*Primary Examiner* — Phuong K Dinh
(74) *Attorney, Agent, or Firm* — Husch Blackwell

(57) ABSTRACT

Disclosed herein is a device configured to impart flavoring to an airstream admitted the device prior to the airstream reaching an aerosol generator of the device, the device thereby operable to deliver a flavored aerosol from an outlet.

20 Claims, 8 Drawing Sheets

Related U.S. Application Data continuation of application No. 16/377,331, filed on Apr. 8, 2019, now Pat. No. 10,674,771, which is a continuation of application No. 15/503,456, filed as application No. PCT/GB2015/052212 on Jul. 31, 2015, now Pat. No. 10,278,427.

(51) Int. Cl.
*A61M 15/06* (2006.01)
*A24F 40/10* (2020.01)
*A24F 40/20* (2020.01)

(56) References Cited

U.S. PATENT DOCUMENTS

| | | |
|---|---|---|
| 3,521,642 A | 7/1970 | Jordan et al. |
| 3,521,643 A | 7/1970 | Toth et al. |
| 3,771,534 A | 11/1973 | Kuehne |
| 4,094,119 A | 6/1978 | Sullivan |
| 4,145,001 A | 3/1979 | Weyenberg et al. |
| 4,161,283 A | 7/1979 | Hyman |
| 4,284,089 A | 8/1981 | Ray |
| 4,480,647 A | 11/1984 | Sprecker et al. |
| 4,503,851 A | 3/1985 | Braunroth |
| 4,917,301 A | 4/1990 | Munteanu |
| 4,947,874 A | 8/1990 | Brooks et al. |
| 4,947,875 A | 8/1990 | Brooks et al. |
| 5,082,008 A | 1/1992 | Johnson |
| 5,167,242 A | 12/1992 | Turner et al. |
| 5,301,694 A | 4/1994 | Raymond et al. |
| 5,388,594 A | 2/1995 | Counts et al. |
| 5,501,236 A | 3/1996 | Hill et al. |
| 5,636,787 A | 6/1997 | Gowhari |
| 5,799,106 A | 8/1998 | Mooney et al. |
| 5,799,663 A | 9/1998 | Gross et al. |
| 6,155,268 A | 12/2000 | Takeuchi |
| 7,100,618 B2 | 9/2006 | Dominguez |
| 7,647,932 B2 | 1/2010 | Cantrell et al. |
| 8,430,106 B2 | 4/2013 | Potter et al. |
| 8,459,271 B2 | 6/2013 | Inagaki |
| 8,997,753 B2 | 4/2015 | Li et al. |
| 9,167,852 B2 | 10/2015 | Xiu |
| 9,352,597 B2 | 5/2016 | Sakaino |
| 9,532,597 B2 | 1/2017 | Tucker et al. |
| 9,642,397 B2 | 5/2017 | Dai et al. |
| 9,814,262 B2 | 11/2017 | Peleg et al. |
| 9,814,263 B2 | 11/2017 | Cochand et al. |
| 9,861,772 B2 | 1/2018 | Terry et al. |
| 10,172,901 B2 | 1/2019 | Spencer et al. |
| 10,278,427 B2 | 5/2019 | Buchberger |
| 10,278,927 B2 | 5/2019 | Hammond et al. |
| 10,701,969 B2 | 7/2020 | Buchberger |
| 11,278,052 B2 | 3/2022 | Mitrev et al. |
| 2004/0221857 A1 | 11/2004 | Dominguez |
| 2005/0268911 A1 | 12/2005 | Cross et al. |
| 2006/0054165 A1 | 3/2006 | Hughes et al. |
| 2006/0196518 A1 | 9/2006 | Hon |
| 2007/0023056 A1 | 2/2007 | Cantrell et al. |
| 2007/0062548 A1 | 3/2007 | Horstmann et al. |
| 2007/0074734 A1 | 4/2007 | Braunshteyn et al. |
| 2007/0102013 A1 | 5/2007 | Adams et al. |
| 2008/0092912 A1 | 4/2008 | Robinson et al. |
| 2008/0110458 A1 | 5/2008 | Srinivasan et al. |
| 2008/0241255 A1 | 10/2008 | Rose et al. |
| 2009/0065011 A1 | 3/2009 | Maeder et al. |
| 2009/0272379 A1 | 11/2009 | Thorens et al. |
| 2011/0120482 A1 | 5/2011 | Brenneise |
| 2011/0226236 A1 | 9/2011 | Buchberger |
| 2011/0290267 A1 | 12/2011 | Yamada et al. |
| 2011/0297166 A1 | 12/2011 | Takeuchi et al. |
| 2012/0204889 A1 | 8/2012 | Xiu |
| 2013/0074857 A1 | 3/2013 | Buchberger |
| 2013/0192623 A1 | 8/2013 | Tucker et al. |
| 2014/0020693 A1 | 1/2014 | Cochand et al. |
| 2014/0166029 A1 | 6/2014 | Weigensberg et al. |
| 2015/0245669 A1* | 9/2015 | Cadieux ............ A24F 40/465 131/329 |
| 2017/0095005 A1 | 4/2017 | Monsees et al. |
| 2017/0112889 A1 | 4/2017 | Spencer et al. |
| 2017/0238611 A1 | 8/2017 | Buchberger |

FOREIGN PATENT DOCUMENTS

| | | |
|---|---|---|
| CN | 1323231 A | 11/2001 |
| CN | 2487392 Y | 4/2002 |
| CN | 101137446 A | 3/2008 |
| CN | 101822420 A | 9/2010 |
| CN | 103393222 A | 11/2013 |
| CN | 103783674 A | 5/2014 |
| DE | 19630619 A1 | 2/1998 |
| DE | 19654945 A1 | 3/1998 |
| DE | 102006039115 A1 | 3/2008 |
| EP | 0150810 A2 | 8/1985 |
| EP | 0836857 A1 | 4/1998 |
| EP | 0822760 B1 | 6/2003 |
| EP | 2481308 A1 | 8/2012 |
| EP | 2625974 A1 | 8/2013 |
| EP | 2431808 B1 | 4/2015 |
| GB | 408856 A | 4/1934 |
| GB | 2488257 A | 8/2012 |
| JP | S62175896 U | 11/1987 |
| JP | H0194861 A | 4/1989 |
| JP | H07184627 A | 7/1995 |
| JP | H0856640 A | 3/1996 |
| JP | H119693 A | 1/1999 |
| JP | 2001507576 A | 6/2001 |
| JP | 2002078476 A | 3/2002 |
| JP | 2009502194 A | 1/2009 |
| JP | 2009509523 A | 3/2009 |
| JP | 2010506594 A | 3/2010 |
| JP | 2013519382 A | 5/2013 |
| JP | 2014500472 A | 1/2014 |
| JP | 2016509852 A | 4/2016 |
| JP | 2017511703 A | 4/2017 |
| KR | 20010020746 A | 3/2001 |
| KR | 100483502 B1 | 4/2005 |
| KR | 20070087265 A | 8/2007 |
| KR | 20080059567 A | 6/2008 |
| KR | 20120053521 A | 5/2012 |
| KR | 20120008751 U | 12/2012 |
| KR | 101314934 B1 | 10/2013 |
| RU | 2297781 C2 | 4/2007 |
| WO | WO-8801884 A1 | 3/1988 |
| WO | WO-9622801 A1 | 8/1996 |
| WO | WO-9828994 A1 | 7/1998 |
| WO | WO-03034847 A1 | 5/2003 |
| WO | WO-2006086655 A1 | 8/2006 |
| WO | 2007042941 A2 | 4/2007 |
| WO | WO-2007039794 A2 | 4/2007 |
| WO | WO-2008108889 A1 | 9/2008 |
| WO | WO-2009135729 A1 | 11/2009 |
| WO | WO-2010045670 A1 | 4/2010 |
| WO | WO-2010095659 A1 | 8/2010 |
| WO | WO-2010095660 A1 | 8/2010 |
| WO | WO-2011109848 A1 | 9/2011 |
| WO | WO-2012078973 A1 | 6/2012 |
| WO | WO-2013050934 A1 | 4/2013 |
| WO | WO-2014097294 A1 | 6/2014 |
| WO | WO-2014110119 A1 | 7/2014 |
| WO | WO-2014140273 A2 | 9/2014 |
| WO | WO-2016005533 A1 | 1/2016 |
| WO | WO-2017109448 A2 | 6/2017 |

OTHER PUBLICATIONS

Extended Search Report for European Application No. 19150425.7, dated Aug. 26, 2019, 20 pages.

Freudenberg Vliesstoffe KG, Vildeon. RTM. Filter Mats, https://www.freudenberg-filter.com/company/brands/viledon/, Apr. 17, 2018, 2 pages.

International Preliminary Report on Patentability for Application No. PCT/AT2011/000122, mailed on Sep. 25, 2012, 7 pages.

(56) References Cited

OTHER PUBLICATIONS

International Preliminary Report on Patentability for Application No. PCT/GB2015/052212, mailed on Nov. 29, 2016, 16 pages.
International Search Report and Written Opinion for Application No. PCT/AT2011/000122, mailed on Aug. 4, 2011, 6 pages.
International Search Report and Written Opinion for Application No. PCT/GB2015/052212, mailed on Oct. 21, 2015, 19 pages.
Japan Tobacco Inc., ZeroStyle.RTM., available at www.jt.com, as retrieved on Apr. 17, 2018, 7 pages.
McNeil Consumer Healthcare Gmbh, "Nicorette.RTM. Inhaler," Retrieved from the Internet: URL: www.nicorette.de, on Apr. 17, 2018, 8 pages.
"Mitsubishi Materials Corporation," Retrieved from the Internet: URL: http://www.mmc.co.jp/corporate/en, on Apr. 17, 2018, 5 pages.
Notice of Allowance mailed Apr. 23, 2021 for Korean Patent Application No. 1020197021114, 3 pages.
Notice of Allowance mailed Mar. 26, 2020 for Japanese Patent Application No. 2018-239020, 2 pages.
Office Action dated Nov. 5, 2018, for Chinese Application No. 201580043507.8, 11 pages.
Office Action for European Application No. 15747208.8, dated Dec. 4, 2017, 8 pages.
Office Action for Japanese Application No. 2017-507765, dated Feb. 4, 2020, 8 pages.
Office Action for Japanese Application No. 2017-507765, dated Jan. 30, 2018, 5 pages (10 pages with translation).
Office Action For Japanese Application No. 2020-078424, mailed on Jun. 29, 2021, 12 pages.
Office Action mailed Apr. 6, 2018 for Korean Application No. 10-2017-7003991, 7 pages (15 pages with translation).
Office Action mailed Apr. 28, 2018 for Russian Application No. 2017104461, 6 pages (10 pages with translation).
Office Action mailed Oct. 29, 2018 for Korean Application No. 10-2017-7003991, 7 pages (13 pages with translation).
Porex Technologies, Porex Custom Plastics, as available at www.porex.com, as retrieved on Apr. 17, 2018, 2 pages.
Red Arrow International LLC, available at www.redarrowinternational.com, as retrieved on Apr. 17, 2018, 1 page.
Search Report mailed Feb. 2, 2015 Great Britain Application No. GB1414331.7, 4 pages.
"Application and File History for U.S. Appl. No. 16/842,153, filed Apr. 7, 2020", (Copy Not Attached).
"Application and File History for U.S. Appl. No. 17/452,435, filed Oct. 27, 2021", (Copy Not Attached).
"Decision to Grant received for European Patent Application No. 15747202.8, mailed on Jan. 7, 2019", 2 pages.
"Intention to Grant received for European Patent Application No. 15747202.8, mailed on Aug. 10, 2018", 7 pages.
"Multi Flavor Generator", China Academic Journal Electronic Publishing House, 1994-2023, 3 pages (2 pages of English Translation and 1 page of Official Copy).
"Notice of Allowance received for Chinese Patent Application No. 201910949890.3, mailed on Jan. 3, 2023", 6 pages (2 pages of English Translation and 4 pages of Official Copy Only).
"Office action received for European Patent Application No. 15747202.8, mailed on Dec. 4, 2017", 8 pages.
"Office Action received for Korean Patent Application No. 10-2021-7022991, mailed on Oct. 19, 2021", 6 pages (Official Copy Only).
"Reasons of Refusal received for Japanese Patent Application No. 2018-17006, mailed on Feb. 4, 2020", 8 pages (4 pages of English Translation and 4 pages of Official Copy).
Buchberger, "Application and File History for U.S. Appl. No. 13/583,365, filed Oct. 23, 2012", (Copy Not Attached).
Buchberger, "Application and File History for U.S. Appl. No. 15/399,121, filed Jan. 5, 2017", (Copy Not Attached).
Buchberger, "Application and File History for U.S. Appl. No. 15/503,456, filed Feb. 13, 2017", (Copy Not Attached).
Buchberger, "Application and File History for U.S. Appl. No. 16/377,331, filed Apr. 8, 2019", (Copy Not Attached).
Martin, et al., "Environmental Tobacco Smoke (ETS): A Market Cigarette Study", Environment International, vol. 23, No. 1, 1997, pp. 75-90.

\* cited by examiner

AEROSOL DELIVERY DEVICE AND METHOD UTILIZING A FLAVORING RESERVOIR

RELATED APPLICATION

This application is a continuation of application Ser. No. 16/842,153, which is a continuation of application Ser. No. 16/377,331 filed Apr. 8, 2019 (now issued as U.S. Pat. No. 10,674,771), which is a continuation of application Ser. No. 15/503,456 filed Feb. 13, 2017 (now issued as U.S. Pat. No. 10,278,427), which in turn is a National Phase entry of PCT Application No. PCT/GB2015/052212, filed Jul. 31, 2015, which claims priority from GB Patent Application No. 1414331.7, filed Aug. 13, 2014, all of which are hereby fully incorporated herein by reference.

TECHNICAL FIELD

The present disclosure relates to an aerosol delivery device and method and in particular but not exclusively to an aerosol delivery device and method that utilize a flavoring reservoir.

BACKGROUND

An aerosol delivery device can be used for generating a nicotine-containing condensation aerosol.

One example of an inhaler is described in US20110226236 which relates to an inhaler component for producing a nicotine-containing steam/air mixture or/and condensation aerosol by evaporation of a nicotine solution which is highly diluted with ethanol or/and water. The inhaler component comprises the following elements: a housing; a chamber arranged in the housing; an air inlet opening for the supply of air from the surroundings to the chamber; an evaporator for evaporating a portion of the highly diluted nicotine solution, the evaporator comprising an evaporation or steam emission surface arranged in the chamber, from which surface the steam produced passes over to the chamber and mixes in the chamber with the air supplied through the air inlet opening, thereby eventually producing the nicotine-containing steam/air mixture or/and condensation aerosol. In order to remove the high solvent diluent in the formed steam/air mixture or condensation aerosol to a maximum possible extent, the inhaler component comprises a two-step solvent removal device which consists of a condensate drainage and storage device communicating with the chamber and of a condenser through which the produced steam/air mixture or/and condensation aerosol can flow.

Another example of an inhaler component is described in WO2011/109848 which relates to an inhaler component having: a housing with a housing jacket; a mouthpiece with a mouthpiece opening for delivering an inhalable medium into the oral cavity of a user; a scent reservoir that is able to communicate with the environment by diffusion and contains a scent, for releasing the scent into the environment and for the olfactory perception of the scent by the user, wherein a) the housing comprises a housing component; b) the mouthpiece is detachably connected to the housing component; c) the housing jacket comprises a first jacket part and a second jacket part; d) the housing component forms the first jacket part; e) the mouthpiece forms the second jacket part, and f) the scent reservoir is structurally combined with the mouthpiece, has a planar configuration and is arranged flat on the second jacket part or itself forms the second jacket part.

A non-heating type tobacco flavor inhaler is described in WO2010/095659. According to this document, a non-heating type tobacco flavor inhaler is provided with an inhalation holder having an inhalation route defined therein, and also with a filled body disposed in the inhalation route. The filled body consists of tobacco grains, and the inhalation route and the filled body provide air flow resistance in the range from about 40 to about 80 mmAq.

Another non-heating type flavor inhaler is described in WO 2010/095660. According to this document, a non-heating type flavor inhaler provided with: an inhalation holder; an upstream region and a downstream region which are defined in the inhalation holder, said upstream region extending from the tip of the inhalation holder up to a partition wall, said downstream region extending, except the upstream region, from the tip of the inhalation holder up to the mouthpiece end and having a front flow path extending along the upstream region; outside air introducing openings formed in the peripheral wall of the inhalation holder and allowing the upstream region and the outside to communicate with each other; and a pouch mounted at the boundary between the upstream region and the downstream region, extending along the longitudinal axis of the inhalation holder, and releasing the flavor of tobacco.

SUMMARY

Viewed from a first aspect, there can be provided an aerosol delivery device comprising: an air inlet; a flavoring reservoir arranged to provide release of flavoring material to air passing therethrough; and an aerosol chamber arranged to provide an aerosol in air passing therethrough; and an aerosol outlet; the air inlet, flavoring reservoir, aerosol chamber and aerosol outlet are arranged in fluid communication in that order. Thus a flavored aerosol can be generated in such manner as to avoid a flavoring reservoir becoming contaminated with aerosol particles and/or condensation of liquid from an aerosol, while at the same time providing that the whole air volume of the flavored aerosol is subjected to both flavoring and aerosol generation.

Viewed from another aspect, there can be provided a device configured to impart flavoring to an airstream admitted the device prior to the airstream reaching an aerosol generator of the device, the device thereby operable to deliver a flavored aerosol from an outlet. Thus a device can create a flavored aerosol by passing a whole air volume through both flavoring and aerosol generation without contaminating a flavoring source with aerosol particles and/or condensate.

Viewed from a further aspect, there can be provided a method of generating a flavored aerosol, the method comprising: imparting flavor to an airflow by passing airflow through a flavor reservoir to cause flavor molecules and/or particles to be carried by the airflow; generating an aerosol by passing the airflow carrying flavor molecules and/or particles through an aerosol generator that evaporates a liquid into the airflow to create a flavored aerosol: and delivering the flavored aerosol to a mouthpiece. Thus a flavored aerosol can be generated in such manner as to avoid a flavoring reservoir becoming contaminated with aerosol particles and/or condensation of liquid from an aerosol, while at the same time providing that the while air volume of the flavored aerosol is subjected to both flavoring and aerosol generation.

BRIEF DESCRIPTION OF THE FIGURES

The present disclosure will now be discussed, by way of example only, with reference to the following drawings in which like reference numerals denote like elements.

Figure 1:
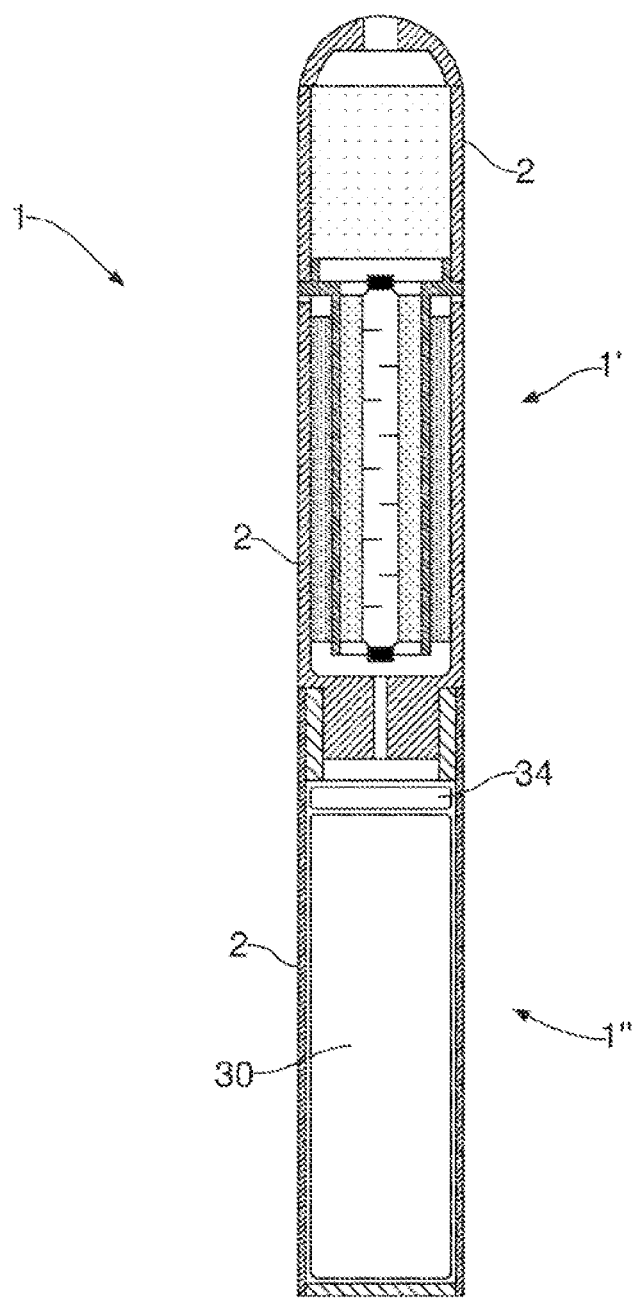
FIG. 1 shows a cross-sectional side view of an aerosol delivery device comprising an aerosol-forming member according to a first example.

While the presently described approach is susceptible to various modifications and alternative forms, specific embodiments are shown by way of example in the drawings and are herein described in detail. It should be understood, however, that drawings and detailed description thereto are not intended to limit the scope to the particular form disclosed, but on the contrary, the scope is to cover all modifications, equivalents and alternatives falling within the spirit and scope as defined by the appended claims

DESCRIPTION

Referring to FIG. 1, there is shown a first example of an aerosol delivery device 1. The aerosol delivery device 1 comprises an aerosol delivery portion 1' and a power portion 1". In the present example, the aerosol delivery portion 1' and power portion 1" are arranged as separate regions of a single, unitary, aerosol delivery device 1 having a single housing 2 that houses both portions. In other examples, the aerosol delivery portion 1' and power portion 1" can be removably connected to enable a given power portion 1" to receive a number of different aerosol delivery portions 1' and/or to enable a given aerosol delivery portion 1' to receive a number of different power portions 1". In such alternative examples, the housing 2 may be openable to enable replacement of one portion or may be divided in correspondence to the division of the portions such that each portion includes its own respective housing part.

The aerosol delivery device 1 may be configured to be re-usable or disposable. In the example in which the aerosol delivery portion 1' and power portion 1" are separable, either or both of the aerosol delivery portion 1' and power portion 1" may be configured as being re-usable or disposable.

The power portion 1" provides a source of electrical power for powering one or more components within the aerosol delivery portion 1'. In the present example, the power portion 1" has with the housing a battery 30. Delivery of power from the battery 30 to the aerosol delivery portion 1' is controlled by electric circuitry 34. In other examples the battery 30 may be replaced by another portable power source such as a capacitive power store such as a supercapacitor or ultracapacitor, a mechanical power source such as a spring or dynamo, or an alternative chemical energy source such as a fuel cell.

Figure 2:
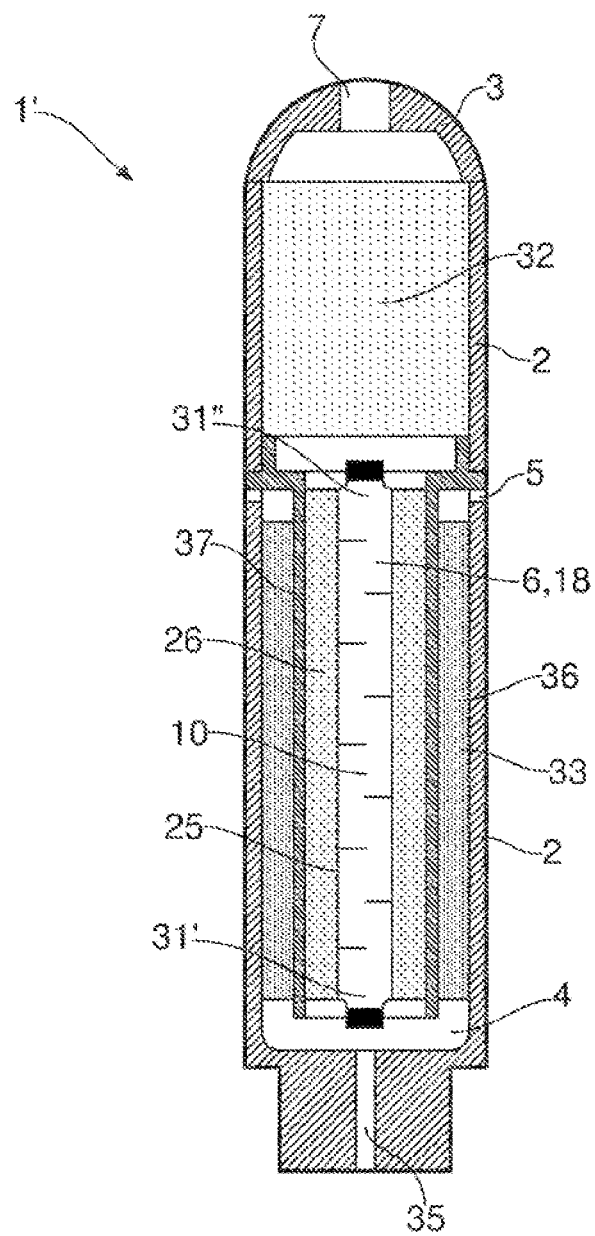
FIG. 2 shows a cross-sectional side view of an aerosol delivery portion of the aerosol delivery device shown in FIG. 1.

FIG. 2 shows the aerosol delivery portion 1' in greater detail. As can be seen from FIG. 2, the aerosol delivery portion 1' is contained within housing 2 and has a mouthpiece 3 at one end and an attachment element at the other end. The attachment element is configured to connect (either permanently or releasably) to the power portion 1". As shown in FIG. 2, the attachment element has a connection member 35 to provide for electrical connection between the power portion 1" and any power utilizing elements of the aerosol delivery portion 1'.

The aerosol delivery portion 1' as shown in FIG. 2 defines a gas pathway therethrough, the gas pathway having an inlet 5, a flavoring reservoir 36, a plenum chamber 4, an aerosol chamber 6 (also referred to as tubular channel 18), refining member 32 and an outlet aperture 7 that extends through the mouthpiece 3. Air can be encouraged to flow through the gas pathway by the application of suction at the mouthpiece 3. Such suction may typically be provided by a user drawing air through the aerosol delivery device 1 when inhaling to receive a delivery of aerosol. In overview, air taken in through the inlet 5 and passing along the gas pathway first picks up flavoring material from the flavoring reservoir 36 before the forming of an aerosol at the aerosol chamber 6 for delivery to the outlet aperture 7. This process will be described in more detail below.

As shown in FIG. 2, the flavoring reservoir 36 provides an inlet passage or channel between the inlet aperture 5 and the plenum chamber 4. In some examples a single inlet 5 may be provided and in other examples a number of inlets 5 may be provided at different points around the circumference of the housing 2. The inlet passage or channel provided by the flavoring reservoir 36 has an annular cross section and encompasses the aerosol chamber 6 and associated aerosol forming member 10. In the configuration of the present example, the air inside the inlet passage and the aerosol inside the tubular channel 18 (aerosol chamber 6) are flowing in opposite directions.

As fresh air moves through the inlet passage it passes over or through the flavoring reservoir 36 which results in the release of flavors. The flavors disperse in the air and are taken downstream together with the air. The flavor enriched/flavored air is then collected in the plenum chamber 4. The plenum chamber 4 acts to provide uniformity to the flow of air to the aerosol chamber 6/tubular channel 18. The air enters the aerosol chamber 6 via an air inlet 31'.

As will be described in more detail below, the aerosol forming member 10 has a chamber wall 25 surrounding the aerosol chamber 6, then a liquid reservoir matrix 26 is arranged outside the chamber wall, with the aerosol chamber 6 having an aerosol chamber inlet 31' and an aerosol chamber outlet 31". Separation between the inlet passage/flavoring reservoir 36 and the liquid reservoir matrix 26 is provided by a support member 37 located between the liquid reservoir matrix 26 and the flavoring reservoir 36. The aerosol forming member 10 uses heat provided by the flow of electrical current to aid the aerosol generation.

In the present example, the flavoring reservoir 36 is located around the aerosol forming member 10. While the heat generated by the heating element of the aerosol forming member 10 is primarily used to vaporize liquid provided from the liquid reservoir matrix 26, a portion of that heat may be used to heat up the flavoring reservoir 36 to an elevated temperature. This secondary or waste heat can be transferred to the flavoring reservoir 36 by thermal conduction through components of the aerosol forming member 10 and support member 37. For example, heat may be conducted through the chamber wall 25, through the liquid reservoir matrix 26 and through the tubular support member 37 holding the aerosol forming member 10 and the liquid reservoir matrix 26, and thereby provided to the flavoring reservoir 36 and the flavors contained therein.

This conductive heat transfer enables the flavoring reservoir 36 to reach temperatures that it would not reach otherwise, enabling enhanced release of flavors inside the reservoir 36. As the release of flavors inside the reservoir 36 is principally by diffusion, and as diffusion is significantly temperature dependent in operation, the amount of temperature elevation achieved in the flavoring reservoir 36 by the conductive heat transfer need not be large to achieve the enhanced release of flavors. In addition to the thermal conductivity properties of the conductive heat transfer path and a heated structure of the reservoir 36, the amount of temperature rise may depend upon a number of factors associated with use of the device 1. For example the length of a given draw or puff through the device 1 may affect the operating time of the heating element and thus the total amount of heat generation that occurs during the draw or puff. Also, the time space between draws or puffs may impact the total temperature rise if that timespan is sufficiently short that at least some components of the device 1 do not cool fully between draws or puffs. In practice a temperature rise on the range of 5° C. to 30° C. is anticipated to be feasible and a rise of as little of 1° C. is expected to provide some enhancement to the release of flavors. For a given implementation of the device, an expected temperature rise can be calculated and measured and in some examples it may be appropriate to tailor the flavors in the flavoring reservoir to the expected temperature rise.

The arrangement of the present example provides that the only gas to enter the flavoring reservoir 36 is air introduced into the device 1 via the inlet aperture(s) 5. Since the flavoring reservoir 36 does not receive vapor or aerosol generated inside the aerosol chamber 6, the surface of flavor providing elements within the flavoring reservoir 36 will not attract or become clogged with condensate or aerosol particles generated at the aerosol chamber 6.

As will be appreciated, the entire air volume drawn in by a user when inhaling to receive a delivery of aerosol (which volume may typically be of the order of 30-80 ml) is provided to the aerosol chamber 6 and can completely be used for generating the aerosol. This can provide for efficient aerosol formation.

The flavoring reservoir 36 may comprise a permeable highly porous wadding or filling material. In the present example, the material completely fills/extends over the channel cross section of the inlet passage or channel in which the flavoring reservoir 36 is arranged. In other examples, the flavoring reservoir 36 may extend over a portion that is less than the whole cross section. The flavoring reservoir 36 may consist of a prefabricated pack or cartridge. In some examples, the flavoring reservoir 36 may comprise or consist of tobacco or tobacco extract. Suitable tobaccos are, in particular, dried fermented tobacco, reconstituted tobacco, expanded tobacco or mixtures of the same. The tobacco may be present as cut tobacco, such as fine cut tobacco, or as fine granulates or tobacco flour. Such forms provide a relatively large surface area to facilitate the release of flavors contained in the tobacco. In another example, the flavoring reservoir 36 may comprise an inert wadding or filling material or another open-pored inert substrate, the surface of which is coated with a flavoring material. The coating may, for example, contain an extract, condensate or distillate of tobacco or tobacco smoke, or a fraction such as a volatile, aromatic or flavorful fraction of the aforementioned extracts, condensates or distillates, or tobacco flour. Any material, such as the examples given above, of a flavoring extracted from or based upon, at least in part, tobacco may be termed a tobacco derivative. The coating can alternatively or additionally contain menthol or an essential oil.

The flavoring substance or material can be a substance insoluble in water and/or glycerol. In the present context, insolubility is indicative of a solubility of less than one percent by weight at 20° C. and 1 atm. Thus, by providing for dispersal of flavorings into the airflow within the flavoring reservoirs, even flavorings that are not water or glycerol soluble can be effectively included in the aerosol provided by the aerosol delivery device.

Thereby a flavoring can be provided to the air entering through the inlet 5. As described above, the release of flavor to the passing air can be facilitated or assisted by heating of the flavoring reservoir 36, for example using the approach of conducting excess heat from the aerosol forming device 10 to the flavoring reservoir 36.

In the present example, the flavoring reservoir 36 is additionally configured as a flow resistor 33. The flow resistor 33 provides the main pressure drop when a user is drawing in air (inhaling through the device 1, also referred to as drawing on the device or puffing on the device 1). The arrangement of the flow resistor 33 can be configured to provide a level of pressure drop appropriate to a particular intended use. In one example, the pressure drop can be configured to correspond to or approximate the pressure drop that would be expected of a conventional (i.e. ignited tobacco type) cigarette. The comparatively large volume of the flavor reservoir 36 can provide flow characteristics that substantially correspond to those of a cigarette. In other examples where the device 1 is configured for delivery of flavoring and/or liquid suspension in aerosol of materials other than those associated with tobacco smoking, an alternative pressure drop may be configured as required for the intended use. The flow characteristics of the arrangement depicted in FIG. 2 are substantially linear, i.e. the pressure drop over the flavoring reservoir 36 is directly proportional to the flow rate through the favoring reservoir 36.

Figure 3:
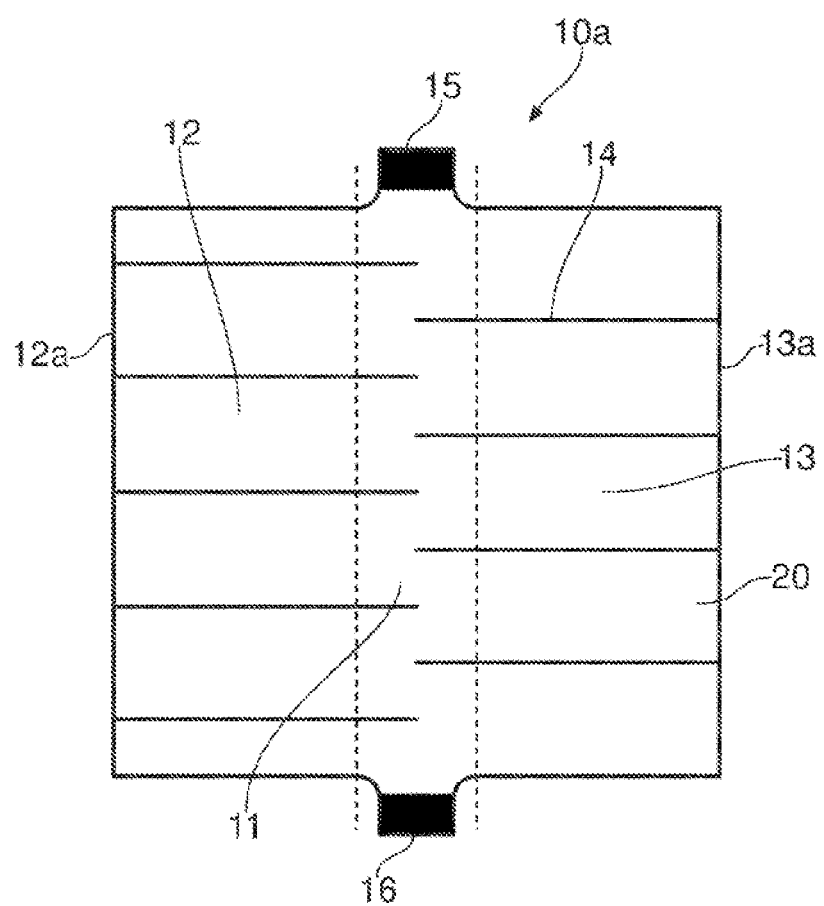
FIGS. 3 to 7 show example aerosol forming members.

FIG. 3 now shows more detail of the aerosol forming member 10a. As shown in FIG. 3, an aerosol-forming member 10a comprises a material that is configured to wick and heat a solution such that the sheet of material can absorb solution and thereafter heat it up such that it evaporates and forms a vapor. The material used in the present examples is sheet-like in nature and comprises two major opposing surfaces 20, 21. The sheet of material may comprise an open-pored structure, foam structure or interconnecting network of pores, all of which form a capillary structure. The capillary structure enables the aerosol-forming member 10a to wick or absorb a solution. The term "capillary structure" used herein is to be understood as a structure through which liquid or a solution can travel as a result of capillary action.

The aerosol-forming member 10a of the present example may be made of a porous, granular, fibrous or flocculent sintered metal(s) so as to form a capillary structure. For instance, Bekipor™ sintered fiber material from Bekaert (www.bekaert.com) falls in this category of materials. In other examples, the aerosol-forming member 10a comprises an open-pored metallic foam or a group of layers of wire mesh or calendered wire mesh which also form capillary structures. The aerosol-forming member 10a may be formed from stainless steel. Furthermore, the aerosol forming member 10a may be formed with a capillary structure that extends throughout the whole aerosol-forming member 10a such that it is exposed on the two major surfaces 20, 21 of the sheet of material. In some examples, one of the major surfaces 20, 21 may be sealed with a metallic foil or cover that is sintered or attached to said major surface. Alternatively, a region of one or both of the major surfaces 20, 21 may be sealed. In another example, the aerosol-forming member 10*a* is configured such that the capillary structure does not extend throughout the whole aerosol-forming member 10*a*. In another example, a thin support layer may be sintered onto one or both of the major surfaces 20, 21. Such a support layer may be formed from a wire mesh made of stainless steel.

The material from which the aerosol-forming member 10*a* is formed is heatable in that it comprises sufficient electrical resistivity so that when current is passed through, the aerosol-forming member 10*a* heats up to a temperature sufficient to cause the solution held in the capillary structure to evaporate or vaporize. Therefore, in the present examples, the aerosol-forming member 10*a* can be considered to comprise a heating element formed with a capillary structure such that the heating element and the capillary structure are integrated and form a single entity or unit.

In the above described examples wherein the sheet of material comprises a single layer configured to wick and heat a solution, the sheet of material can be described as comprising a heating element and a wick that are arranged in the same surface.

Additionally, the aerosol-forming member 10*a* may comprise any combination of the aforementioned structures and materials, e.g. by providing multiple layers of different structures/materials, the layers being joined together, e.g. by sintering.

In one such example, the aerosol-forming member 10*a* comprises a sheet of material that is sheet-like in nature and formed from a plurality of layers. For example, the aerosol-forming member 10*a* may comprise a first heatable layer acting as a heating element. This first layer is formed from a material that is configured to be heated up. This first layer may be formed from a metal, such as stainless steel. The aerosol-forming member 10*a* may further comprise a second layer formed with an open-pored structure, foam structure or interconnecting network of pores, all of which form a capillary structure. The capillary structure enables the aerosol-forming member 10*a* to wick or absorb a solution. This second layer may be made of a porous, granular, fibrous or flocculent material so as to form the capillary structure. Alternatively, the second layer may comprise an open-pored foam, fabric or a group of mesh layers forming the capillary structure. The second layer may be made of a non-conductive material such as glass, carbon or ceramic. This second layer acts as a wick. The first layer (heating element) and the second layer (wick formed with a capillary structure) are laid on top of each other so as to form a sheet of material having two opposing major surfaces, wherein the capillary structure may be exposed on one or both of the major surfaces. In this example, the sheet of material can be described as comprising a heating element and a wick arranged in parallel surfaces. In one example, the first layer may be formed of a metal wire mesh or metal foil and the second layer may be formed of a glass fiber structure or fabric fritted onto or otherwise attached to the first layer.

In another example, the first layer also comprises a capillary structure as described above with reference to the second layer, such that the first layer can both heat and wick a solution. In this example, the sheet of material can be described as comprising a heating element and a wick that are arranged in the same surface and in parallel surfaces.

In another example, the sheet of material comprises a third layer that is similar to the second layer in that it comprises a capillary structure. The second and the third layer sandwich the first layer such that the capillary structure is exposed on both major surfaces of the sheet of material.

The sheet of material according to any of the above described examples has a thickness or depth that typically falls within the range of 20-500 μm. In some examples, the thickness falls within the range of 50 to 200 μm. The thickness or depth should be understood as meaning the distance between the two major surfaces 20, 21 of the sheet of material.

Figure 4:
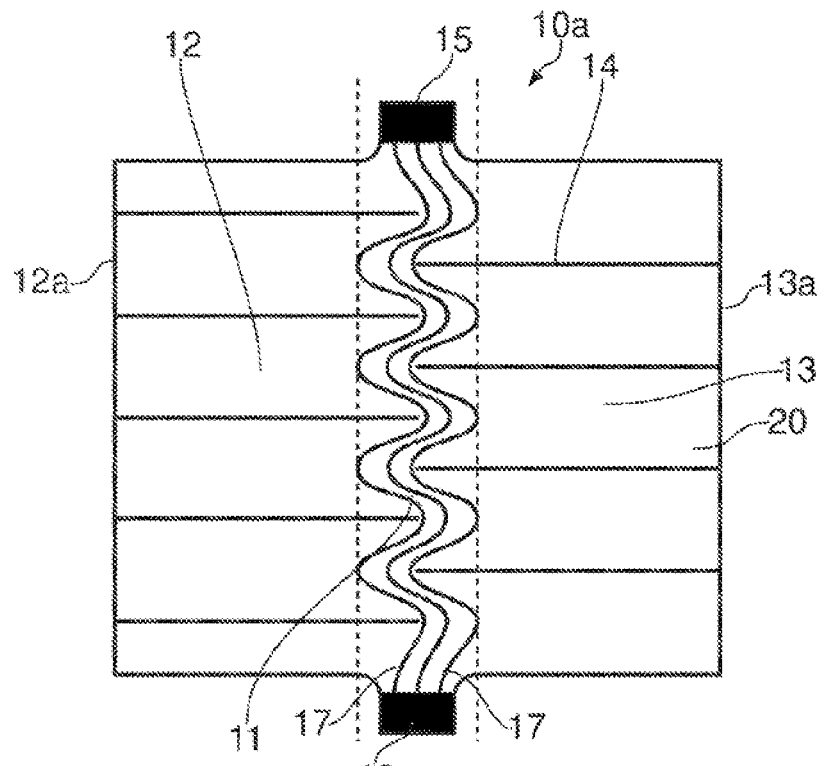
Figure 6:
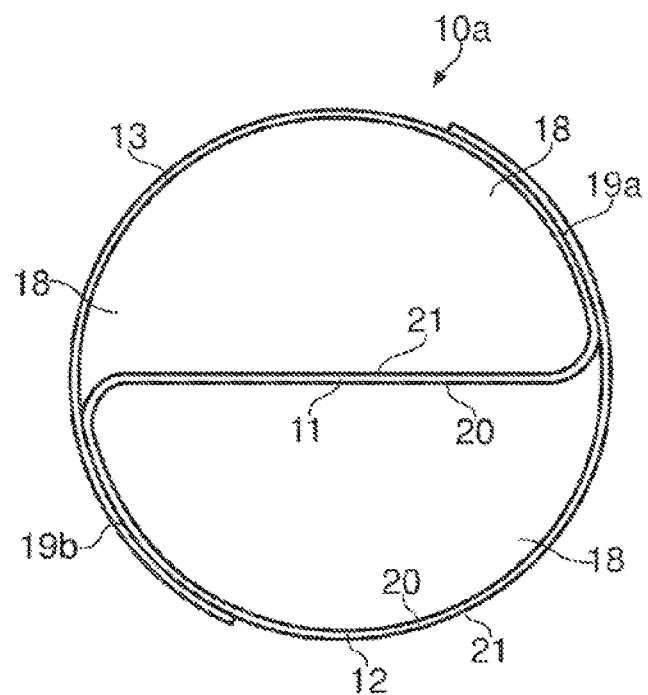

FIGS. 3 and 4 show the aerosol-forming member 10*a* in an unfolded state or position and FIG. 6 shows the aerosol-forming member 10*a* in a folded state or position. The sheet of material has a first or central section 11 and a second and a third section 12, 13 on either side of the central section 11. The dashed lines in FIG. 3 represent the boundaries between the sections 11, 12, 13. The second 12 and third 13 sections are formed with slots or notches 14 that extend from opposing long edges 12*a*, 13*a* of the aerosol-forming member 10*a* towards and into the first section 11. In the arrangement shown in FIG. 3, the second section 12 is formed with five slots 14 and the third section 13 is formed with four slots 14, although other configurations of numbers of slots are possible. The slots 14 as illustrated in FIG. 3 are approximately parallel to one another and spaced apart across the second and third sections 12, 13.

Opposing free ends of the first section 11 act as electrical terminals 15, 16. The electrical terminals 15, 16 are configured to be electrically connected, e.g. via an electric circuitry 34, to a power source, such as the battery 30, so that an electric current can be passed across the aerosol-forming member 10*a*. The electrical terminals 15, 16 may extend from the first section as seen in FIG. 2 enabling them to slot into connection holes (not shown) of the aerosol delivery device, the connection holes being electrically connected to the power source. Alternatively, an electrically conductive wire connected to the power source may be clipped, soldered or welded onto each electrical terminals 15, 16 so that a current can be passed across the aerosol-forming member 10*a*. In some examples, the electrical terminals are in line with adjacent edges of the second and third sections 12, 13 such that the terminals do not protrude. These terminals may be connected to an electrically conductive wire via a clip and/or the wire may be soldered or welded onto the terminals. It should also be understood that the electrical terminals may be of any other shape and it is envisaged that other means suitable for connecting the electrical terminals to the power source may be used.

When a current is passed through the aerosol-forming member 10*a*, the slots 14 compress the electric field 17 such that it is substantially contained within the first section 11 as illustrated in FIG. 4. The dashed lines in FIG. 4 represent boundaries between the first, second and third sections 11, 12, 13. As a result, the first section 11 is primarily or directly heated up whilst the second and third sections 12, 13 remain relatively unheated, although some heat generated by the current passing through the first section 11 is expected to cause some heating of the second and third sections 12, 13. Heat that is generated in or which is conducted to the second and third sections 12, 13 can then be onwardly conducted to provide a small level of heating to the flavoring reservoir 36 as described above. Additionally or alternatively heat may be transferred to the flavor reservoir by one or more of radiation heat originating from the heated first section 11 and absorbed by the chamber wall, and condensation heat released from vapor condensing on chamber wall 25. The heat transferred to the flavoring reservoir can be thought of as secondary heat or waste heat as such heat is not directly used for generating the aerosol.

Figure 5:
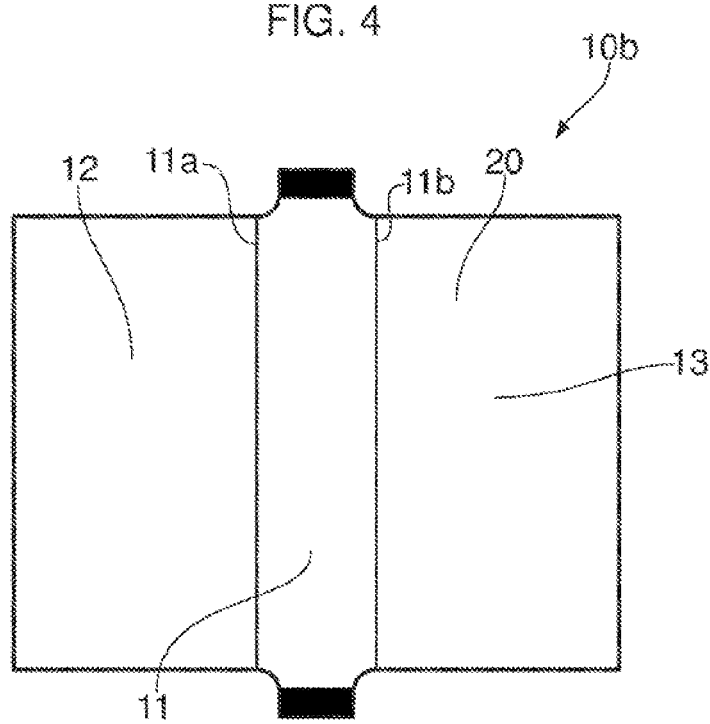

The present teachings are however not limited to an aerosol-forming member 10*a* comprising slots so as to contain the heat within the first section 11. An example of such an arrangement is shown in FIG. 5, where the sheet of material comprises discrete sections with different material properties. The first section 11 is made of a material of low electrical resistivity whereas the second or the third sections 12, 13 are formed from a material with high electrical resistivity such that when a potential difference is applied between the terminals 15, 16, an current will primarily pass through the first section 11. It should be understood that the first section 11 may also be formed with a capillary structure such that it extends throughout the whole aerosol-forming member 10*a*. The difference in electrical resistivity results in that the first section 11 heats up relatively to the second and third sections 12, 13.

An example of such an embodiment is wherein the sheet of material comprises a non-conductive fiber web or fabric made of glass or carbon fibers, glass or carbon fiber yarns or any other non-conductive and inert fiber materials. The fiber web or fabric provides the capillary structure and extends throughout all sections of the sheet of material. Conductive fibers or wires are incorporated in the fiber web or fabric in a first or central section of the sheet of material making said first or central section heatable. The conductive fibers or wires may be made of stainless steel or of a heating wire alloy like Chromium Nickel. Alternatively, conductive fibers may replace non-conductive fibers and conductive wires (heating wires) may replace non-conductive yarns.

Thus it will be understood that a variety of constructions consistent with the present teachings are possible to achieve primary heating of a first section 11 to facilitate aerosol generation and to achieve secondary heating by way of conduction of heat from the aerosol forming member 10*a* to the flavor reservoir.

Referring now to FIG. 6, there is shown the aerosol-forming member 10*a* in a folded state or position. The second and third sections 12, 13 are folded about the first section 11 such that the second and third sections 12, 13 enclose the first section 11 and form a channel 18. Regions 19*a*, 19*b* of the second and third sections 12, 13 overlap such that the channel 18 is completely enclosed in a direction about the first section 11. The first section 11 is substantially planar or flat and suspended in the channel 18 such that it extends across the channel 18.

It should be understood that the second and third sections 12, 13 do not have to form a tubular channel 18. In alternative examples the second and third sections 12, 13 are folded about the first section 11 such that they form a channel having an oval, square, rectangular or any other type of polygonal cross-section.

It should also be appreciated that the first section 11 is not limited to being planar or fat. In an alternative example, the first section 11 comprises corrugations having ridges and grooves such that it follows a meandering or oscillating path, or a sinusoidal curve. The ridges and grooves may extend in a direction parallel to the opposing long edges 12*a*, 13*a* of the sheet of material.

Figure 7:
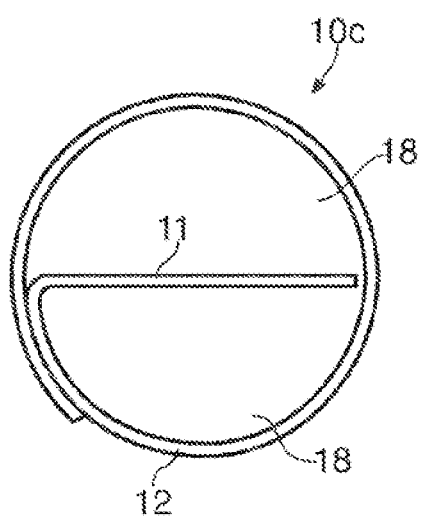

In another example, as shown in FIG. 7, the third section 13 is omitted such that the aerosol-forming member 10*c* has a first section 11 and a second section 12. The second section 12 extends from the first section 11 and folds about the first section 11 such that the second section 12 forms a channel 18 and the first section 11 is suspended across the channel 18. Alternatively, the second section 12 partially encloses the first section 11. For example, the second section 12 may extend around a single surface of the first section 11 such that the cross-section of the aerosol-forming member 10*a* has a semi-circular shape.

Figure 8:
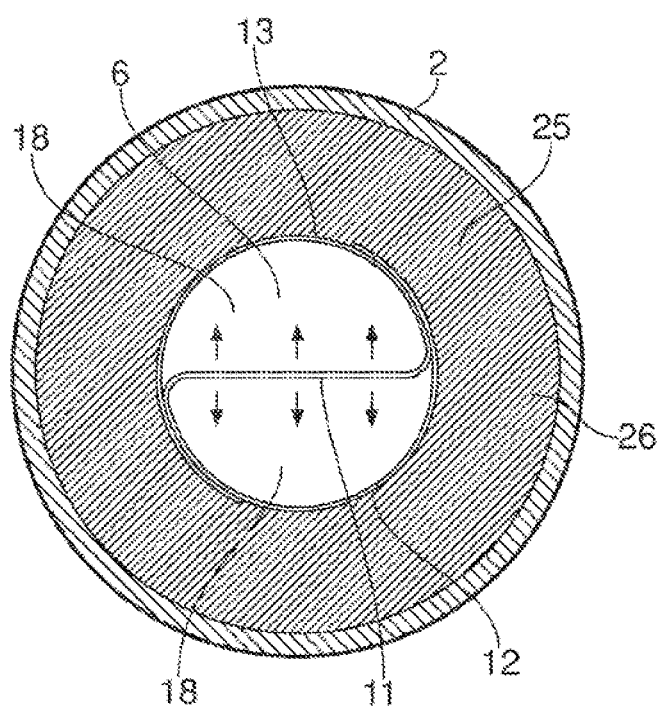
FIG. 8 shows an example aerosol-forming member located in an aerosol chamber.

Referring now to FIG. 8, the aerosol-forming member 10*a* is located in the aerosol chamber 6. The aerosol forming member 10*a* thus defines the chamber wall 25 adjacent or proximal a liquid reservoir matrix. The chamber wall 25 therefore may be expected to be at a boundary edge of the structure making up the reservoir matrix. The liquid reservoir matrix 26 comprises a capillary structure, for example an interconnecting porous or open-porous structure, such that it can hold a solution or liquid. The liquid reservoir matrix 26 may be formed from a fiber material, for example polyethylene or polyester fibers. In an example where heat is to be provided to the flavoring reservoir 36 by conduction of secondary heat from the aerosol forming member 10*a*, the liquid reservoir may be configured to provide conduction of the secondary heat. This may be provided by the reservoir matrix itself being thermally conductive or may be provided by thermally conductive elements passing through or around the reservoir matrix.

The shape of the aerosol chamber 6 defined by the chamber wall 25 corresponds to the shape of the aerosol-forming member 10*a*. In the arrangement shown in FIG. 8, the second and third sections 12, 13 contact the liquid reservoir matrix 26. In other examples, it may be that only one of the second and third sections 12, 13 contacts the liquid reservoir matrix 26. Alternatively, if the aerosol-forming member 10*a* only comprises a second section 12 as seen in FIG. 7 then only the second section 12 is in contact with the liquid reservoir matrix 26. It should also be understood that it is not necessary for the whole second and/or third sections 12, 13 to contact the liquid reservoir matrix 26. For example, only a portion of the second and/or third sections 12, 13 may contact the liquid reservoir matrix 26. In such examples it may be the case that surface sections of the liquid reservoir matrix 26 (not in contact with sections 12, 13) effectively form sections of the chamber wall 25. In another example the aerosol-forming member 10*a* may contact the liquid reservoir matrix 26 only via the outer edges of sections 12, 13. In this example the chamber wall 25 is completely formed by the liquid reservoir matrix 26.

As will be appreciated, the aerosol chamber 6 and aerosol forming member 10*a* may be constructed in any appropriate manner that provides for aerosol formation as air passes through a chamber. Thus as an alternative, so-called atomizers based upon use of a heating coil wound around a fiber wick may be used.

As is illustrated in FIG. 8, the first section 11 is located across the aerosol chamber 6.

Advantageously, the liquid reservoir matrix 26 does not have to be made out of a heat resistant material as it is shielded from the heat of the first section 11 by the second and/or third sections 12, 13 that are not substantially heated up during operation of the aerosol delivery device 1. The secondary heat conducted through or across the reservoir matrix is of sufficiently small magnitude that special thermal resistance is not expected to be required, The liquid reservoir matrix 26 holds a solution that is formed into aerosol by the aerosol-forming member 10*a*. The solution is drawn or absorbed into the aerosol-forming member 10*a* by capillary action via the capillary structure of the second and the third sections 12, 13. The solution is spread throughout the capillary structure of the aerosol-forming member 10a, i.e. the first, second and third sections 11, 12, 13. When the first section 11 is heated up, the solution evaporates from the first section 11 so as to form a vapor which upon condensation forms an inhalable aerosol. Thereafter, and even during the heating, the first section 11 is replenished with solution by capillary action moving solution from the liquid reservoir matrix 26, via the second and third sections 12, 13 to the first section 11. This is described in more detail below.

The capillarity of the aerosol-forming member 10a may be greater than the capillarity of the liquid reservoir matrix 26 so as to induce flow of solution from the liquid reservoir matrix 26 towards the aerosol-forming member 10a. The capillarity is defined by the pore size and the wetting conditions of the respective capillary structures.

As previously described, the power source enabling the aerosol-forming member 10a to heat up may be a battery 30. The battery 30 is controlled by the electric circuitry 34 which include a controller and may be mounted on a printed circuit board (PCB). Examples of illustrative circuit structures are shown in FIGS. 9a and 9b.

Figure 9A:
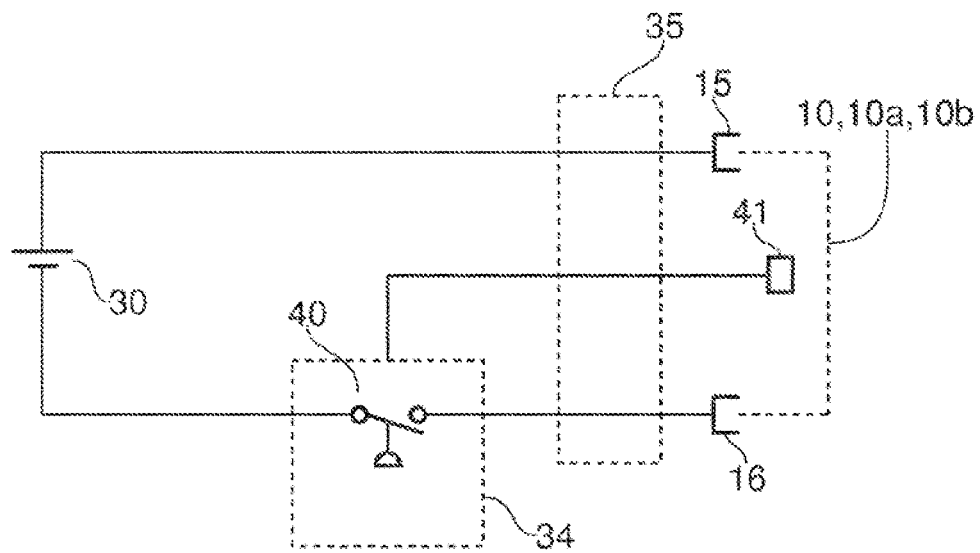
FIGS. 9a and 9b show example control circuits.

As is shown in FIG. 9a, the electrical terminals 15, 16 of the aerosol-forming member 10a are electrically connected to the positive and negative terminals of the battery 30 respectively as previously described. Control of electrical current to the terminals 15, 16 is provided by the electrical circuit 34. The circuit of this example includes a pressure-activated switch 40 that activates responsive to a signal from a pressure sensor 41. The pressure sensor 41 is arranged to detect a pressure alteration when a user commences inhaling through the aerosol delivery device 1. The pressure sensor 41 may for example be arranged in fluid communication with the plenum chamber 4 in order to detect the pressure change. Although it is indicated in FIG. 9 that the pressure sensor 41 is connected to the electric circuit 34 via the connection member 35, it is also possible to arrange the pressure sensor 41 at the electric circuit 34 and to provide fluid communication between the plenum chamber 4 and the pressure sensor 41 via a passage extending through the connection member 35. The signal from the pressure sensor 41 then activates the switch 40 (either directly or via a controller) so as to allow a flow of current from the battery 30 to the terminals 15, 16. The switch 40 may be an electrical switch such as a power-MOSFET switching circuit activatable responsive to the signal from the pressure sensor 41. The switch 40 and any control circuitry therefor may be provided at a PCB of the electric circuit 34.

Figure 9B:
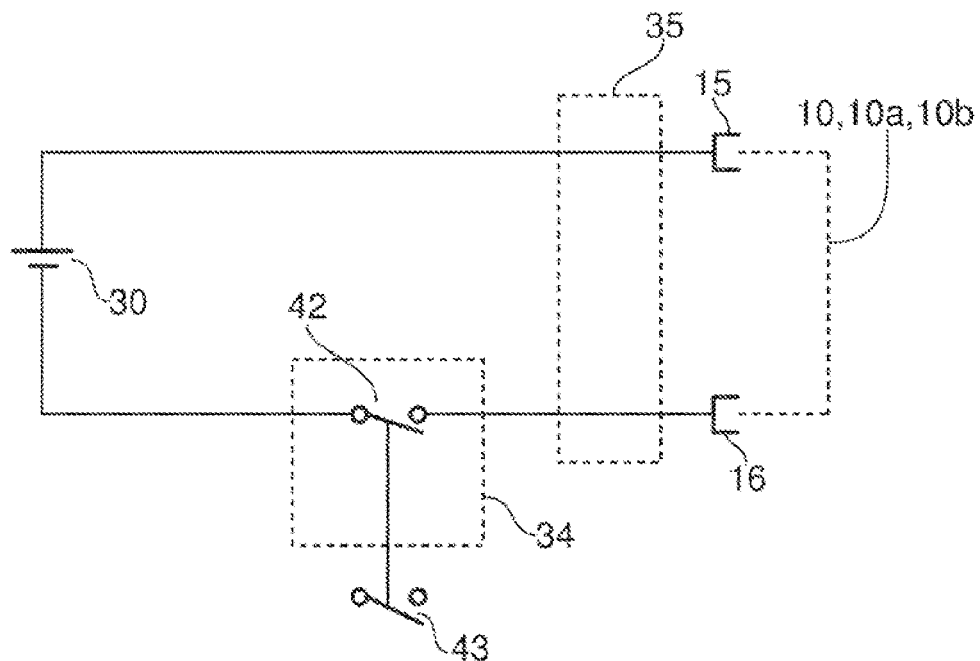

As shown in the example of FIG. 9b, the control of the supply of current from the battery 30 to the terminals 15, 16 may be controlled via a switch 42 that activates responsive to a user-activated switch 43. The user-activated switch 43 may be located at an accessible position on or recessed into the housing 2. The switch 42 may be activated based upon a direct connection to the user-activated switch 43. Alternatively, a control circuit may be provided to control the switch 42 responsive to activation of the user-activated switch 43. The switch 42 may be an electrical switch such as a power-MOSFET switching circuit activatable responsive to the signal from the user-activatable switch 43. The switch 42 and any control circuitry therefor may be provided at a PCB of the electric circuit 34.

In addition, the switching circuit may additionally provide automatic control of the temperature, for example, by using temperature sensors to enable the supply of current to be stopped once a threshold temperature is reached. The switching circuit may additionally or alternatively provide automatic control of duration, to enable the supply of current to be stopped once a threshold activation time is reached.

In some examples, the circuit 34 may be configured to very low or zero power requirements other than when the switch is activated to indicate that provision of current to the terminals 15, 16 is required.

When current is drawn from the battery 30 and through the sheet of material, the electrical resistance of the sheet of material causes the first section 11 of the sheet of material to increase in temperature. In the embodiment wherein the sheet of material comprises several layers, the resistance of the conductive layer acting as a heating element causes the first section 11 to increase in temperature, which in turn heats up the adjacent non-conductive second and/or third layers of the first section 11.

Operation of the aerosol delivery device 1 will now be described with reference to FIGS. 1 and 8. In use, the user may manually activate the aerosol delivery device 1 (for example see the arrangement of FIG. 9b) or the aerosol delivery device 1 may be activated automatically (for example see FIG. 9a) as the user starts to inhale through the aerosol delivery device 1. In either approach, the battery 30 provides a potential difference between the electrical terminals 15, 16 of the aerosol-forming member 10a as the aerosol delivery device 1 is activated, causing current to flow between the electrical terminals 15, 16 such that the first section 11 of the sheet of material increases in temperature. The heat is substantially contained within the first section 11 due to the slots 14, although it should be appreciated that the heat may be contained within the first section 11 by other means as described above. It will also be appreciated that secondary heat may be conveyed to the flavoring reservoir 36 as described above. This increase in temperature at the first section 11 causes the solution held in the capillary structure of the first section 11 of the sheet of material to evaporate so as to form a vapor. The vapor mixes with air drawn into the aerosol delivery device 1 via inlet 5, flavoring reservoir 36, plenum chamber 4 and chamber inlet 31' by suction caused by a user inhaling through the device 1. The vapor mixes with air in the aerosol chamber 6, and as this occurs the vapor condenses and forms droplets such that an inhalable aerosol is produced.

The aerosol-forming member 10a according to any of the above described embodiments is located in the housing such that the planes of the major surfaces 20, 21 are parallel to or substantially aligned with the direction of the airflow through the aerosol chamber 6. Thus, when a solution is held in the aerosol-forming member 10a and it is heated up such that the solution evaporates, the solution evaporates in a direction transverse to the direction of the airflow. In the embodiments wherein the capillary structure is exposed on both sides of the sheet of material, the solution is evaporated from both sides in opposite directions as indicated by the arrows in FIG. 8. The vapor mixes with air so as to form aerosol in the channel 18 formed by the second and/or third sections 12, 13. The channel 18 directs the flow of aerosol through the aerosol delivery device 1 towards the user.

When the aerosol forming device 1 is activated, it is likely that excess vapor will form and then condense onto the chamber wall 6 formed by the second and/or third sections 12, 13 of the aerosol-forming member 10a. The condensation heat released may thus provide a source of heat for transfer to the flavor reservoir; the condensate will be reabsorbed into the capillary structure of sections 12, 13 and resupplied to section 11 of the aerosol-forming member 10a by capillary action as discussed above. In addition to any such condensation heat, the supply of secondary or waste heat to the flavoring reservoir 36 may also be provided by conductive heat transferred within the aerosol forming member 10a from the high temperature section 11 to the adjacent cooler sections 12, 13. Further, the supply of secondary or waste heat to the flavoring reservoir 36 may also be provided by radiation heat transferred from the high temperature section 11 to the adjacent cooler sections 12, 13. Heat rays can cross the aerosol chamber 6 and are then absorbed on the chamber wall 25 formed by sections 12, 13. All three sources of heat together are expected to be active to some extent, with the relative ratio therebetween being dependent upon the exact device configuration. Together these mechanisms provide the secondary or waste heat. This waste heat is passed through or around the liquid reservoir matrix 36 so as to reach the flavoring reservoir 36 for heating the flavoring contained therein.

After the aerosol-forming member 10a has been activated and aerosol has formed in the channel 18, the aerosol is drawn through the channel 18 as the user continues to inhale. The aerosol then exits the aerosol chamber 6 through a chamber outlet 31" as seen in FIG. 2. The aerosol then passes through an optional aerosol refining member 32 provided in the housing 2, causing the aerosol to be cooled. The refining member 32 may also contain further flavoring agents such as menthol that are released into the flow of aerosol before entering the user's mouth via the outlet aperture 7 provided in the mouthpiece 3. Meanwhile, the solution that has evaporated from the capillary structure of the first section 11 of the sheet of material is replaced by fresh solution from the liquid reservoir matrix 26 due to the capillary effect of the capillary structure as described above and the second and/or third section 12, 13 being in contact with the liquid reservoir matrix 26. Fresh air enters the channel 18 via the inlet aperture 5, flavoring reservoir 36, plenum chamber 4 and chamber inlet 31'. In some examples, a pressure drop element or flow resistor 33 is provided so that the flow of air into the aerosol chamber 6 can be controlled. The flow resistor 33 may consist of a simple aperture or hole and may be identical with the inlet aperture 5 in the housing 2. Alternatively the flow resistor 33 may consist of a porous body similar to a cigarette filter providing the flow resistance of a conventional cigarette. In some examples the flow resistor 33 may be provided by the material as discussed above that provides a structure for holding or providing the flavoring within the flavoring reservoir 36. In such examples this material thus provides dual functionality of flavor carrying and flow restriction.

Thus there have now been described examples of implementing the operation and structure of an aerosol delivery device that utilizes secondary heat from an aerosol generation structure to warm a flavoring source to facilitate distribution of flavoring from the flavoring source to incoming air before that incoming air reaches the aerosol generation structure.

Figure 10:
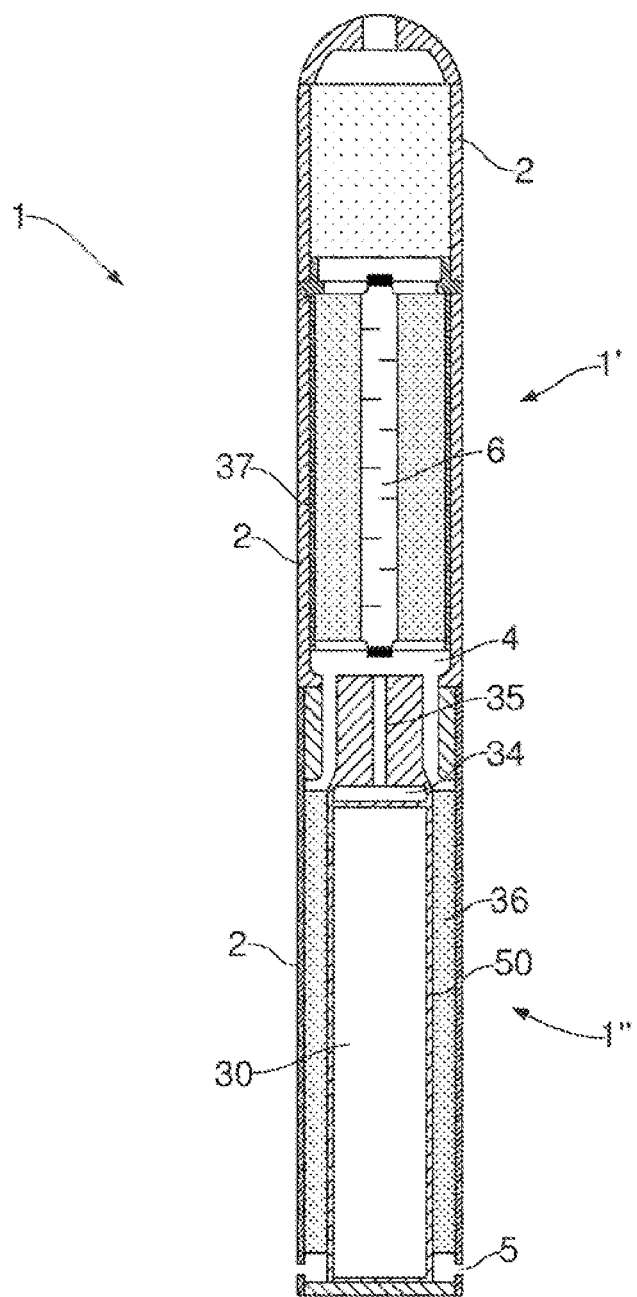
FIG. 10 shows cross-sectional side view of an aerosol delivery device comprising an aerosol-forming member according to another example.

FIG. 10 illustrates another example of an aerosol delivery device 1. The aerosol delivery device 1 comprises an aerosol delivery portion 1' and a power portion 1". In the present example, the aerosol delivery portion 1' and power portion 1" are arranged as separate regions of a single, unitary, aerosol delivery device 1 having a single housing 2 that houses both portions. In other examples, the aerosol delivery portion 1' and power portion 1" can be removably connected to enable a given power portion 1" to receive a number of different aerosol delivery portions 1' and/or to enable a given aerosol delivery portion 1' to receive a number of different power portions 1". In such alternative examples, the housing 2 may be openable to enable replacement of one portion or component (such as a power source 30) or may be divided in correspondence to the division of the portions such that each portion includes its own respective housing part.

The aerosol delivery device 1 may be configured to be re-usable or disposable. In the example in which the aerosol delivery portion 1' and power portion 1" are separable or openable, either or both of the aerosol delivery portion 1' and power portion 1" may be configured as being re-usable or disposable.

In this example, the portably power source 30 (which may be a battery or other portably power source as discussed with reference to FIG. 1 above) does not use the full diameter of the housing 2, but rather has located thereabout (either wholly surrounding or adjacent in part) the gas pathway from the inlet 5 to the plenum chamber 4. As in the previous examples, this gas pathway has arranged therein a flavoring reservoir 36. The flavoring reservoir 36 operates in the same manner as that discussed with reference to FIGS. 1 and 2 above, save in the arrangements for warming of the flavoring reservoir 36.

As in the example described above, as fresh air moves through the inlet passage it passes over or through the flavoring reservoir 36 which results in the release of flavors. The flavors disperse in the air and are taken downstream together with the air. The flavors flavor enriched/flavored air is then collected in the plenum chamber 4. The plenum chamber 4 acts to provide uniformity to the flow of air to the aerosol chamber 6/tubular channel 18. In the configuration of the present example, the air inside the inlet passage and the aerosol inside the tubular channel 18 (aerosol chamber 6) are flowing in like directions but are separated by axial offset between the center of flow through the inlet passage and tubular channel and by the plenum chamber 4.

In the example of FIG. 10, two options for transfer of heat to the flavoring reservoir 36 can be employed, either independently or in combination.

In the first of these options, the property of many batteries to experience a slight temperature increase when supplying current is utilized. Thus, when the portable power supply 30 is a battery or other power supply that tends to experience a temperature increase when supplying current, the heat generated by the power supply 30 may be used to provide the supply of heat to the flavoring reservoir 36 arranges about or adjacent the power supply 30.

The second of these options utilizes a separate heat generation that provides heat for the flavoring reservoir 36 other than by way of conducting secondary heat from the aerosol forming member 10. Such separate heat generation could be provided by providing for the control circuit 34 to allow a low of current through one or more conductive structures in or adjacent to the flavoring reservoir 36 at the same time as the provision of current to the aerosol forming member 10.

As in the example described above, this conductive heat transfer enables the flavoring reservoir 36 to reach temperatures that it would not reach otherwise, enabling enhanced release of flavors inside the reservoir 36.

Thus there have now been described examples of implementing the operation and structure of an aerosol delivery device that utilizes secondary heat from an aerosol generation structure or an alternative heat source to warm a flavoring source to facilitate distribution of flavoring from the flavoring source to incoming air before that incoming air reaches the aerosol generation structure. It will be seen that the examples presented provide a compact structure.

It will be appreciated that implementations may also be provided in which no addition heat provision is made to the flavoring source and instead the incoming air is passed through the flavoring reservoir without heating of the flavoring reservoir before the air reaches the aerosol generation structure.

The above described embodiments of the aerosol-forming member 10 of the aerosol delivery device 1 are described for use with a solution. It should be understood that this solution may comprise certain constituents or substances that may have a stimulatory effect on the user. These constituents or substances may be of any kind that is suitable for being delivered via inhalation. The solution in which the constituents or substances are held or dissolved may primarily consist of water, ethanol, glycerol, propylene glycol or mixtures of the aforementioned solvents. By means of a sufficiently high degree of dilution in an easily volatile solvent, such as ethanol and/or water, even substances which are otherwise difficult to evaporate can evaporate in a substantially residue-free manner, and thermal decomposition of the liquid material can be avoided or significantly reduced.

It should be understood that the term "channel" used herein is not limited to a specific cross-section. Furthermore, the channel may be completely enclosed about the longitudinal axis of the channel, however it should also be appreciated that the channel may not be enclosed but open along a section parallel to the longitudinal axis of the channel.

It is also envisaged that the aerosol-forming member 10 according to any of the embodiments described above may be oxidized or coated with a non-conductive material so as to prevent a short circuit.

This disclosure shows by way of illustration various embodiments in which the present teachings may be practiced and provide for an aerosol-forming member, aerosol delivery device component and aerosol delivery device. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. In addition, the disclosure includes other teachings not presently claimed, but which may be claimed in future.

The invention claimed is:

1. An aerosol delivery device comprising:
   an air inlet;
   a flavoring reservoir arranged to provide release of flavoring material to air passing therethrough;
   an aerosol chamber, and an aerosol forming member arranged to generate an aerosol in air passing through the aerosol chamber;
   an aerosol outlet; and
   a tubular channel for directing the aerosol from the aerosol forming member to the aerosol outlet, wherein the flavoring reservoir is arranged at least partially about, or at least partially surrounds, the tubular channel;
   wherein the flavoring reservoir, aerosol chamber and aerosol outlet are arranged in fluid communication in that order.

2. The aerosol delivery device of claim 1, further comprising an inlet passage, between the air inlet and the tubular channel, for delivering air from the air inlet to the aerosol forming member and the tubular channel, wherein the tubular channel is offset from the inlet passage.

3. The aerosol delivery device of claim 1, wherein the tubular channel is parallel to the inlet passage.

4. The aerosol delivery device of claim 1, wherein the aerosol outlet is in fluid communication with a mouthpiece outlet arranged to deliver an aerosol therethrough when suction is applied to the mouthpiece.

5. The aerosol delivery device of claim 1, wherein the aerosol forming member comprises a heating element arranged to generate a condensation aerosol.

6. The aerosol delivery device of claim 5, further comprising a liquid reservoir in fluid communication with the heating element and arranged to deliver liquid to the heating element, the heating element arranged to generate an aerosol by evaporation of liquid therefrom.

7. The aerosol delivery device of claim 5, the flavoring reservoir in conductive thermal communication with the heating element.

8. The aerosol delivery device of 1, further comprising a switch to provide activation of the aerosol forming member responsive to a flow of air from the inlet toward the outlet.

9. The aerosol delivery device of claim 1, the flavoring reservoir in conductive thermal communication with a heat source.

10. The aerosol delivery device of claim 1, the flavoring reservoir comprising a flavoring carrier and a flavoring material.

11. The aerosol delivery device of claim 10, wherein the flavoring material is insoluble in one or more selected from the group comprising: water and glycerol.

12. The aerosol delivery device of claim 1, the flavoring reservoir comprising tobacco or a tobacco derivative.

13. The aerosol delivery device of claim 10, the flavoring reservoir in conductive thermal communication with the heating element and the flavoring carrier in conductive thermal communication with the heating element or heat source.

14. The aerosol delivery device of claim 1, further comprising a flow resistor upstream of the aerosol forming member.

15. The aerosol delivery device of claim 14, the flow resistor providing a pressure drop proportional to the flow rate through the flow resistor.

16. An aerosol delivery device comprising:
    an air inlet;
    a flavoring reservoir arranged to provide release of flavoring material to air passing therethrough;
    an aerosol chamber, and an aerosol forming member arranged to generate an aerosol in air passing through the aerosol chamber;
    an aerosol outlet;
    a tubular channel for directing the aerosol from the aerosol forming member to the aerosol outlet; and
    an inlet passage, between the air inlet and the tubular channel, for delivering air from the air inlet to the aerosol forming member and the tubular channel, wherein the inlet passage surrounds, and is parallel to the tubular channel;
    wherein the flavoring reservoir, aerosol chamber and aerosol outlet are arranged in fluid communication in that order.

17. An aerosol delivery consumable, removably connectable to a power portion for powering the aerosol delivery aerosol delivery consumable, comprising:
- an air inlet;
- a flavoring reservoir arranged to provide release of flavoring material to air passing therethrough;
- an aerosol chamber, and an aerosol forming member arranged to generate an aerosol in air passing through the aerosol chamber;
- an aerosol outlet; and
- a tubular channel for directing the aerosol from the aerosol forming member to the aerosol outlet, wherein the flavoring reservoir is arranged at least partially about, or at least partially surrounds, the tubular channel;
- wherein the flavoring reservoir, aerosol chamber and aerosol outlet are arranged in fluid communication in that order.

18. An aerosol delivery consumable, removably connectable to a power portion for powering the aerosol delivery aerosol delivery consumable, comprising:
- an air inlet;
- a flavoring reservoir arranged to provide release of flavoring material to air passing therethrough;
- an aerosol chamber, and an aerosol forming member arranged to generate an aerosol in air passing through the aerosol chamber;
- an aerosol outlet;
- a tubular channel for directing the aerosol from the aerosol forming member to the aerosol outlet; and
- an inlet passage, between the air inlet and the tubular channel, for delivering air from the air inlet to the aerosol forming member and the tubular channel, wherein the inlet passage surrounds, and is parallel to, the tubular channel;
- wherein the flavoring reservoir, aerosol chamber and aerosol outlet are arranged in fluid communication in that order.

19. An assembly comprising the aerosol delivery consumable according to claim 17, further comprising the power portion.

20. An assembly comprising the aerosol delivery consumable according to claim 18, further comprising the power portion.

* * * * *